(12) United States Patent
Xu et al.

(10) Patent No.: US 9,708,319 B1
(45) Date of Patent: Jul. 18, 2017

(54) SYNTHESIS OF PARP INHIBITOR TALAZOPARIB

(71) Applicant: Yong Xu, San Diego, CA (US)

(72) Inventors: Yong Xu, San Diego, CA (US); Peter W Yohi, San Diego, CA (US); Michael Xu, San Diego, CA (US); Douglas Cruise, San Diego, CA (US)

( * ) Notice: Subject to any disclaimer, the term of this patent is extended or adjusted under 35 U.S.C. 154(b) by 0 days.

(21) Appl. No.: 15/181,348

(22) Filed: Jun. 13, 2016

(51) Int. Cl.
*C07D 471/06* (2006.01)

(52) U.S. Cl.
CPC .................................. *C07D 471/06* (2013.01)

(58) Field of Classification Search
None
See application file for complete search history.

(56) References Cited

FOREIGN PATENT DOCUMENTS

| WO | 2010/017055 | * | 2/2010 |
| WO | 2015/069851 | * | 5/2015 |
| WO | 2016/019125 | * | 2/2016 |

* cited by examiner

*Primary Examiner* — Emily Bernhardt
(74) *Attorney, Agent, or Firm* — Kile Park Reed & Houtteman LLC

(57) ABSTRACT

Provided is a new method for preparing PARP inhibitor talazoparib.

13 Claims, No Drawings

SYNTHESIS OF PARP INHIBITOR TALAZOPARIB

FIELD

The present disclosure relates to a chemical medicine field, it relates generally to the synthesis of PARP inhibitor talazoparib. Specifically, the disclosure relates to the process for preparation of talazoparib and intermediates thereof.

BACKGROUND

Talazoparib (BMN-673) is a poly (ADP-ribose) polymerase (PARP) inhibitor which blocks PARP by selective binding and prevents PARP-mediated DNA repair of single strand DNA breaks via the base-excision repair pathway. This enhances the accumulation of DNA strand breaks, promotes genomic instability and eventually leads to apoptosis. BMN673 is indicated for the treatment of hematological malignancies, genetically defined solid tumors and metastatic breast cancer. After trials for advanced hematological malignancies and for advanced or recurrent solid tumors. It is now in phase 3 for metastatic germline BRCA mutated breast cancer. Trial estimated to complete in June 2016.

Talazoparib is described chemically as (8S,9R)-5-fluoro-8-(4-fluorophenyl)-9-(1-methyl-1H-1,2,4-triazol-5-yl)-2,7,8,9-tetrahydro-3H-pyrido[4,3,2-de]phthalazin-3-one, and has the structural formula shown as Formula 1:

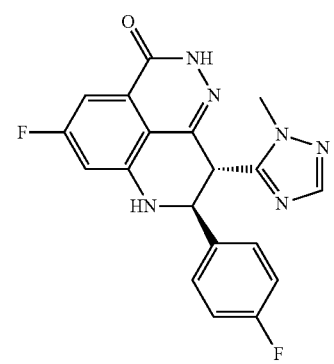

1

International patent application publication No. WO 2010/017055 discloses dihydropyridophthalazinone inhibitors of poly (ADP-ribose) polymerase (PARP). 4-amino-6-fluoroisobenzofuran-1(3H)-one and 4-fluorobenzaldehyde are used as starting materials for preparation of talazoparib; and the reaction of the chiral separation is arranged in the final step, and the chiral separation is performed using super-fluid chromatography (SFC) with chiral column and methanol and CO$_2$ as the eluents, which seriously reduces the yield of the final product.

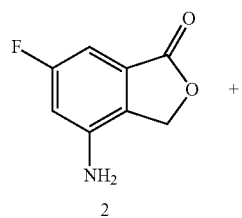

2

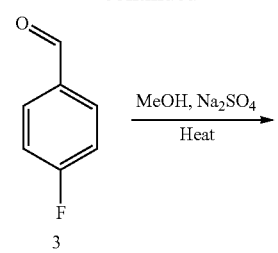

3

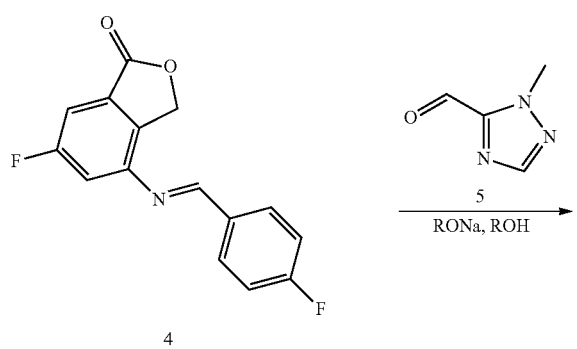

4

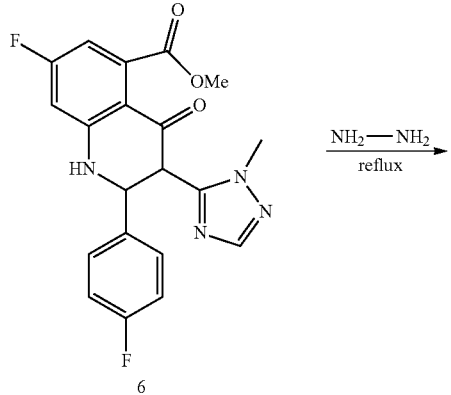

6

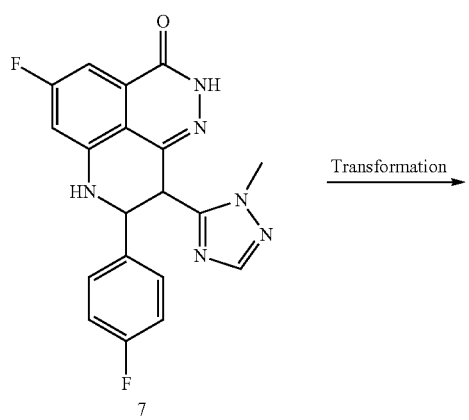

7

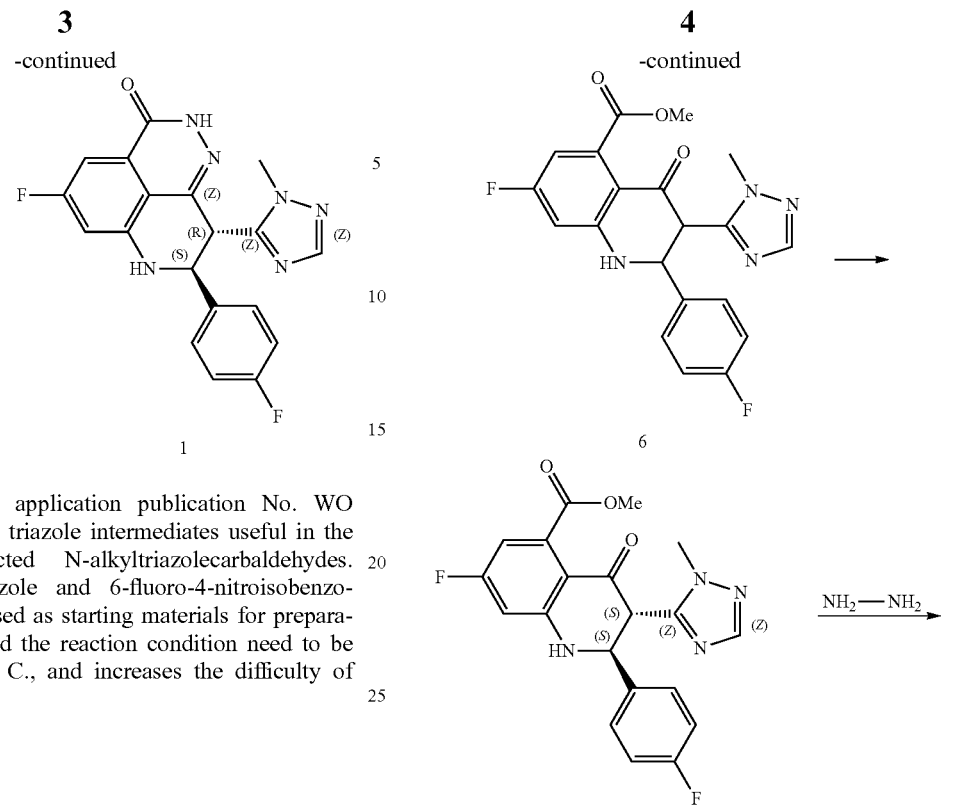

International patent application publication No. WO 2015/069851 discloses triazole intermediates useful in the synthesis of protected N-alkyltriazolecarbaldehydes. 1-methyl-1H-1,2,4-triazole and 6-fluoro-4-nitroisobenzofuran-1(3H)-one are used as starting materials for preparation of talazoparib; and the reaction condition need to be cooled to about −30° C., and increases the difficulty of industrial production.

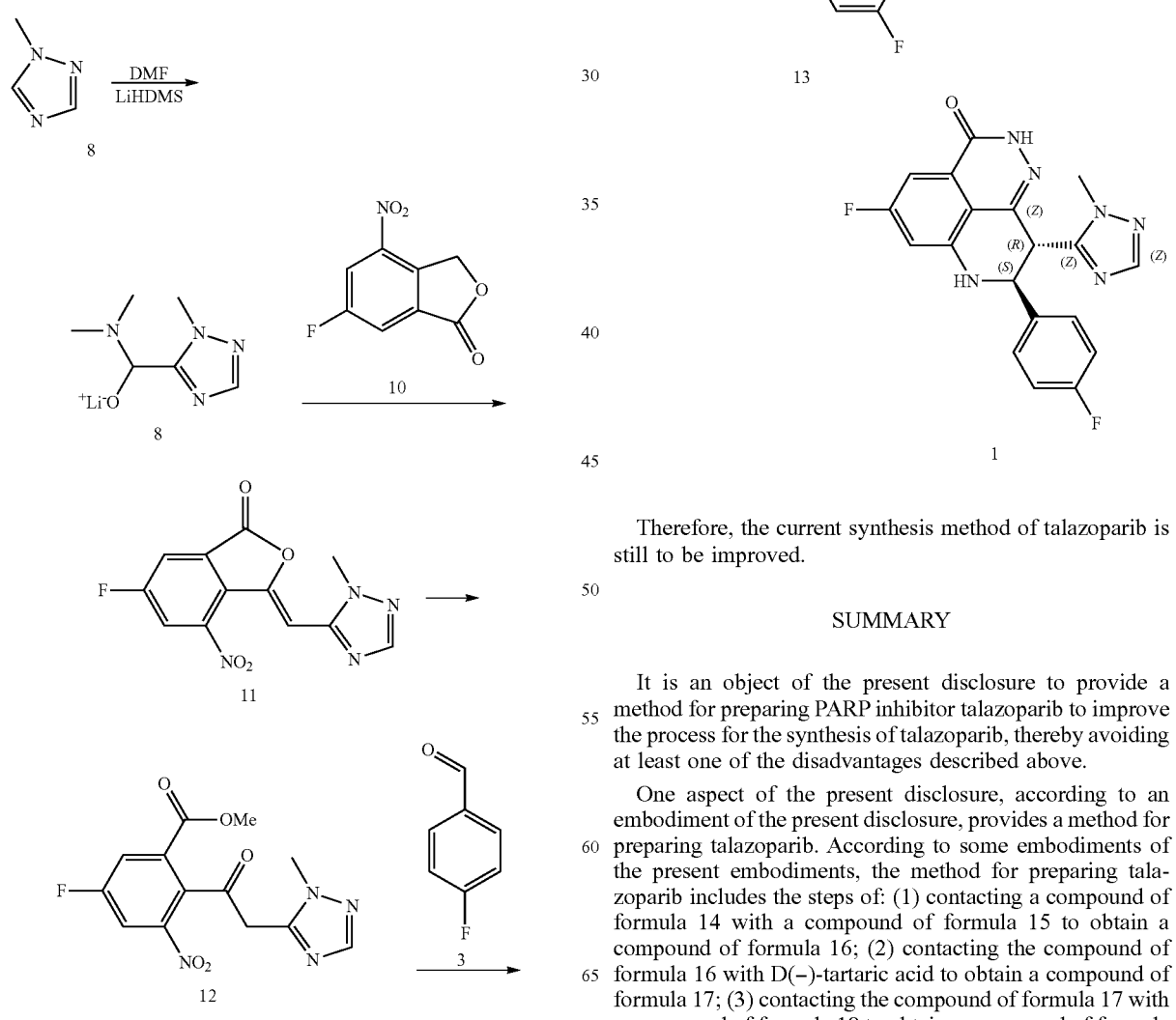

Therefore, the current synthesis method of talazoparib is still to be improved.

SUMMARY

It is an object of the present disclosure to provide a method for preparing PARP inhibitor talazoparib to improve the process for the synthesis of talazoparib, thereby avoiding at least one of the disadvantages described above.

One aspect of the present disclosure, according to an embodiment of the present disclosure, provides a method for preparing talazoparib. According to some embodiments of the present embodiments, the method for preparing talazoparib includes the steps of: (1) contacting a compound of formula 14 with a compound of formula 15 to obtain a compound of formula 16; (2) contacting the compound of formula 16 with D(−)-tartaric acid to obtain a compound of formula 17; (3) contacting the compound of formula 17 with a compound of formula 18 to obtain a compound of formula 13; and (4) contacting the compound of formula 13 with 50% hydrazine hydrate to obtain the compound of formula 1,

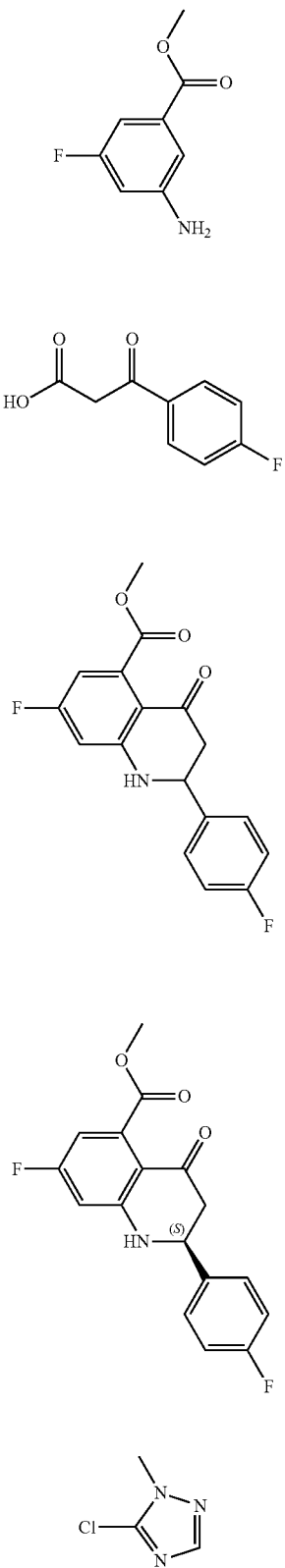

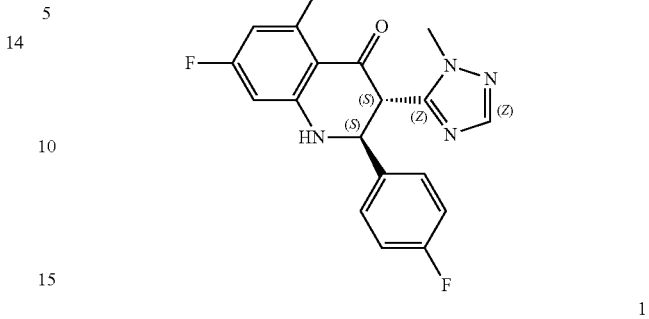

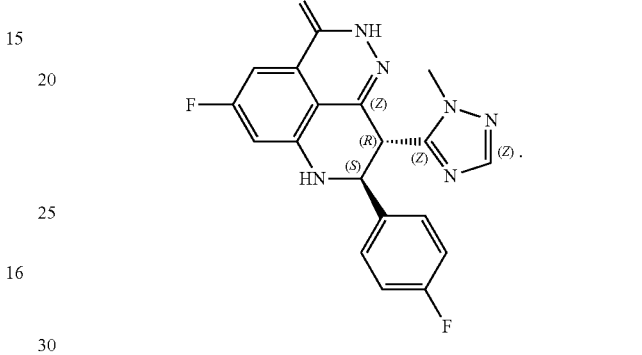

The invention has the advantages of short reaction steps, simple operation, no metal catalyst, no need of low temperature, and is suitable for industrial production.

According to some embodiments of the present embodiments, in the step (1), the compound of formula 14, the compound of formula 15 and dioxane are added into a first reactor, then pyridinium p-toluenesulfonate (PPTS) and MgSO₄ are added into the first reactor, then the first reactor is heated to reflux and stirred for 2 hours to 4 hours, cooled down to 50° C.; NaBH₄ is added into the mixture and heated to 80° C., the first reactor is then stirred for 2 hours to 4 hours; after the reaction, the first reactor is cooled down to room temperature, methanol is added into the first reactor and white solid is filtered; the filtrate is concentrated and extracted by ethyl acetate, then washed with saturated NaHCO₃ aqueous solution and sodium chloride aqueous solution; the organic phase is dehydrated with anhydrous sodium sulfate, filtered and concentrated to obtain crude product; the crude product is purified by column chromatography to give compound 16.

According to some embodiments of the present embodiments, the amount of compound 15 is 1.0 equivalent to 1.3 equivalents per 1 equivalent by mole of the compound of formula 14, so as to improve the synthetic yield of the compound of formula 16.

According to some embodiments of the present embodiments, the amount of PPTS is 0.15 equivalent to 0.3 equivalent per 1 equivalent by mole of the compound of formula 14, so as to improve the synthetic yield of the compound of formula 16.

According to some embodiments of the present embodiments, the amount of NaBH₄ is 3 equivalents to 5 equivalents per 1 equivalent by mole of the compound of formula 14, so as to improve the synthetic yield of the compound of formula 16.

According to some embodiments of the present embodiments, the amount of $MgSO_4$ is 4 equivalents to 6 equivalents per 1 equivalent by mole of the compound of formula 14, so as to improve the synthetic yield of the compound of formula 16.

According to some embodiments of the present embodiments, in the step (2), the compound of formula 16, absolute ethyl alcohol and D(−)-tartaric acid are added into a second reactor, then the second reactor is heated to reflux for 2 hours and then cooled down to obtain white solid; the white solid is filtered off and washed with ethyl alcohol and saturated sodium bicarbonate aqueous solution; the organic phase is dehydrated with anhydrous sodium sulfate, filtered and concentrated to give compound 17.

According to some embodiments of the present embodiments, the amount of D(−)-tartaric acid is 0.52 equivalent to 0.98 equivalent per 1 equivalent by mole of the compound of formula 16, so as to improve the ee value (ee %) of the compound of formula 17.

According to some embodiments of the present embodiments, in the step (3), compound 17 is dissolved in anhydrous tetrahydrofuran at room temperature and stirred, then sodium alcoholate is added into a third reactor; the third reactor is heated to reflux and stirred for 1 hour to 2 hours; the compound of formula 18 is dissolved in tetrahydrofuran and added into the third reactor; the third reactor is stirred for 2 hours to 4 hours and cooled down to room temperature; water is added into the system under ice-bath and the resulting mixture is extracted by ethyl acetate, then washed with saturated sodium bicarbonate aqueous solution and sodium chloride aqueous solution; the organic phase is dehydrated with anhydrous sodium sulfate, filtered and concentrated to give compound 13.

According to some embodiments of the present embodiments, the amount of sodium alcoholate is 1.01 equivalents to 2.0 equivalents per 1 equivalent by mole of the compound of formula 17, so as to improve the synthetic yield of the compound of formula 13.

According to some embodiments of the present embodiments, the amount of the compound of formula 18 is 1 equivalent to 1.6 equivalents per 1 equivalent by mole of the compound of formula 17, so as to improve the synthetic yield of the compound of formula 13.

According to some embodiments of the present embodiments, in the step (4), the compound of formula 13, ethanol and 50% hydrazine hydrate are added into a fourth reactor and heated to reflux for 2 hours to 4 hours; then the solvent is removed by distillation under reduced pressure and the crude product is washed with water, filtered, washed with ethanol and recrystal to give the talazoparib of formula 1.

According to some embodiments of the present embodiments, the amount of 50% hydrazine hydrate is 4 equivalents to 6 equivalents per 1 equivalent by mole of the compound of formula 13, so as to improve the synthetic yield of the talazoparib of formula 1.

DETAILED DESCRIPTION

The term "contacting" herein should be understood broadly, allowing any of at least two reactants react; for example, two reactants to be mixed under appropriate condition. According to the experimental requirements, mixing the reactants with which need to be contacted under stirring. Therefore, the type of agitation is not particularly limited. For example, may be a mechanical agitation, i.e. under the action of mechanical forces stirring.

As used herein, "a compound of formula N" is sometimes also referred to "Compound N". For example, "a compound of formula 2" may also be referred to "compound 2".

In this article, the term "first" or "second" is only used for describing objective other than indicate or imply relative importance or implicit indicate the number of technical features or technical solutions. Thus, defining the "first", the "second" features may explicitly or implicitly includes one or more of the characteristics. In the description of the disclosure, "multiple" means two or more, unless otherwise specifically limited.

According to the present disclosure, it is devised a process of preparing a compound of formula 1:

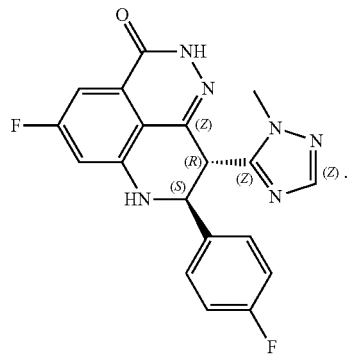

The technical solutions of the present disclosure include: a compound of formula 16 is prepared by a process comprising reacting a compound of formula 14 with a compound of formula 15, a compound of formula 17 is prepared by a process comprising reacting the compound of formula 16 with D(−)-tartaric acid, a compound of formula 13 is prepared by a process comprising reacting the compound of formula 17 with a compound of formula 18, the compound of formula 1 is prepared by a process comprising reacting the compound of formula 13 with 50% hydrazine hydrate.

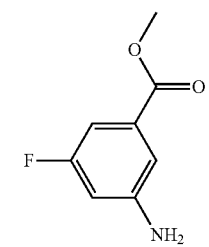

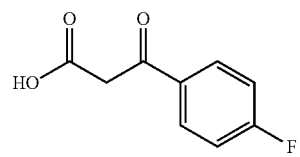

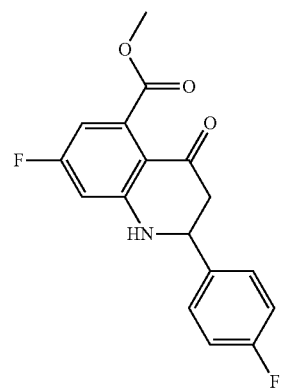

-continued

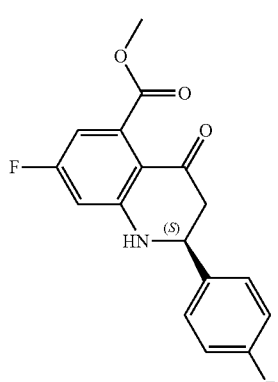

17

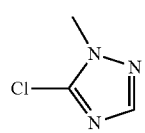

18

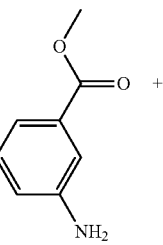

13 reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16.

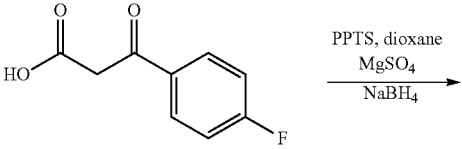

14

15

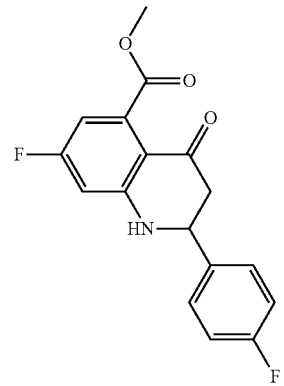

16

According to some embodiments of the present disclosure, a method for preparing a compound of formula 1 includes the following steps:

Step (1): a compound of formula 14 is contacted with a compound of formula 15 to give a compound of formula 16.

Step (2): the compound of formula 16 is contacted with D(−)-tartaric acid to give a compound of formula 17.

Step (3): the compound of formula 17 is contacted with a compound of formula 18 to give a compound of formula 13.

Step (4): the compound of formula 13 is contacted with 50% hydrazine hydrate to give the compound of formula 1.

In some embodiments, in the method disclosed herein, the preparation method of the present invention is as follows.

According to some embodiments of the present disclosure, in the step (1) of the method, the compound of formula 14, the compound of formula 15 and dioxane were added into a first reactor, then pyridinium p-toluenesulfonate (PPTS) and MgSO$_4$ were added into the first reactor, then the first reactor was heated to reflux and stirred for 2 hours to 4 hours, cooled down to 50° C. NaBH$_4$ was added into the mixture and heated to 80° C., the first reactor was then stirred for 2 hours to 4 hours. After the reaction, the first According to some embodiments of the present disclosure, a molar ratio between the compound of formula 14 and the compound of formula 15 is 1: (1.0-1.3) in the step (1). In other embodiments, the molar ratio between the compound of formula 14 and the compound of formula 15 is 1:1.0 in the step (1).

According to some embodiments of the present disclosure, a molar ratio between the compound of formula 14 and PPTS is 1: (0.15-0.3) in the step (1). In other embodiments, the molar ratio between the compound of formula 14 and PPTS is 1:0.2 in the step (1).

According to some embodiments of the present disclosure, a molar ratio between the compound of formula 14 and NaBH$_4$ is 1: (3-5) in the step (1). In other embodiments, the molar ratio between the compound of formula 14 and NaBH$_4$ is 1:4 in the step (1).

According to some embodiments of the present disclosure, a molar ratio between the compound of formula 14 and MgSO₄ is 1: (4-6) in the step (1). In other embodiments, the molar ratio between the compound of formula 14 and MgSO₄ is 1:5 in the step (1).

According to some embodiments of the present disclosure, in the step (2) of the method, compound 16, absolute ethyl alcohol and D(-)-tartaric acid were added into a second reactor, then the second reactor was heated to reflux for 2 hours and then cooled down to obtain white solid. The white solid was filtered off and washed with ethyl alcohol and saturated sodium bicarbonate aqueous solution. The organic phase was dehydrated with anhydrous sodium sulfate, filtered and concentrated to give compound 17.

drofuran and added into the third reactor. The third reactor was stirred for 2 hours to 4 hours and cooled down to room temperature. Water was added into the system under ice-bath and the resulting mixture was extracted by ethyl acetate, then washed with saturated sodium bicarbonate aqueous solution and sodium chloride aqueous solution. The organic phase was dehydrated with anhydrous sodium sulfate, filtered and concentrated to give compound 13.

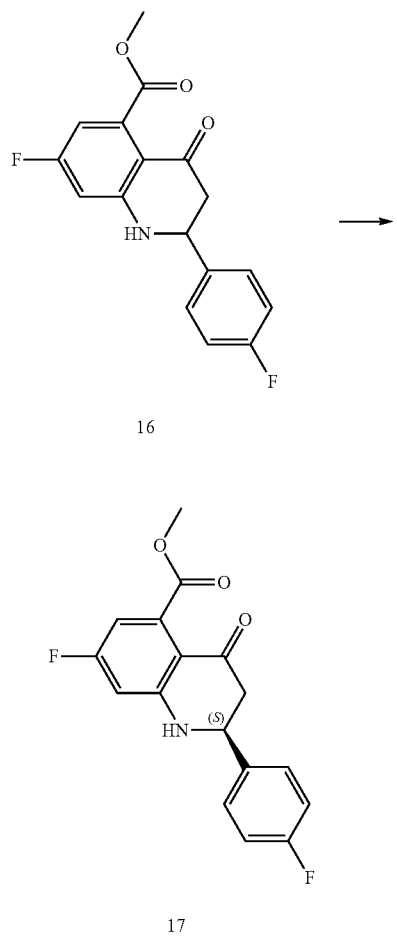

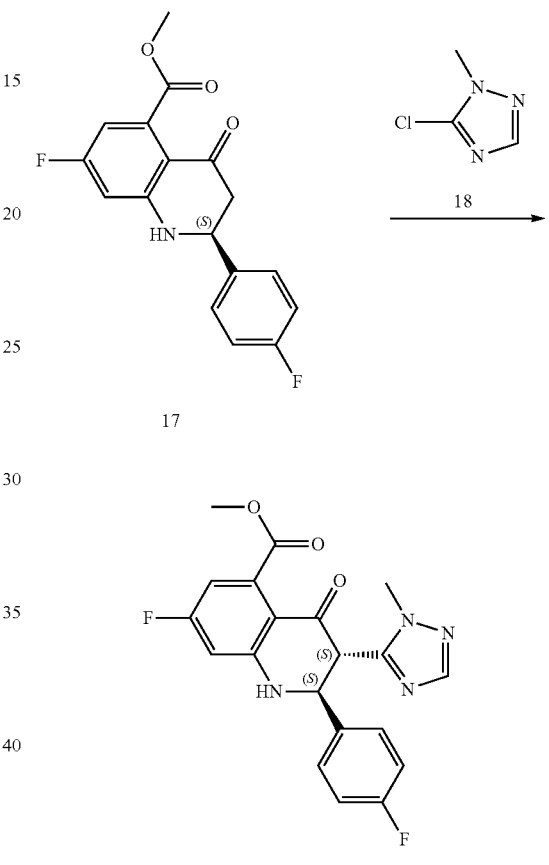

According to some embodiments of the present disclosure, a molar ratio between the compound of formula 16 and D(-)-tartaric acid is 1: (0.52-0.98) in the step (2). In other embodiments, the molar ratio between the compound of formula 16 and D(-)-tartaric acid is 1:0.55 in the step (2).

According to some embodiments of the present disclosure, in the step (3) of the method, compound 17 was dissolved in anhydrous tetrahydrofuran at room temperature and stirred, then sodium alcoholate was added into a third reactor. The third reactor was heated to reflux and stirred for 1 hour to 2 hours. Compound 18 was dissolved in tetrahy- According to some embodiments of the present disclosure, a molar ratio between the compound of formula 17 and sodium alcoholate is 1: (1.01-2.0) in the step (3). In other embodiments, the molar ratio between the compound of formula 17 and sodium alcoholate is 1:1.5 in the step (3).

According to some embodiments of the present disclosure, a molar ratio between the compound of formula 17 and the compound of formula 18 is 1: (1-1.6) in the step (3). In other embodiments, the molar ratio between the compound of formula 17 and the compound of formula 18 is 1:1 in the step (3).

According to some embodiments of the present disclosure, in the step (4) of the method, compound 13, ethanol and 50% hydrazine hydrate were added into a fourth reactor and heated to reflux for 2 hours to 4 hours. Then the solvent was removed by distillation under reduced pressure and the crude product was washed with water, filtered, washed with ethanol and recrystal to give the talazoparib of formula 1.

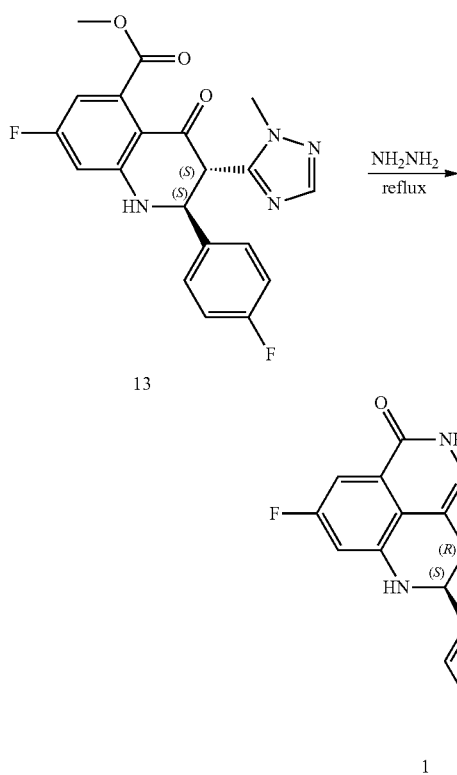

According to some embodiments of the present disclosure, a molar ratio between the compound of formula 13 and 50% hydrazine hydrate is 1: (4-5) in the step (4). In other embodiments, the molar ratio between the compound of formula 13 and 50% hydrazine hydrate is 1:5 in the step (4).

In the present invention, the term "comprise" is an open expression, it means comprising the contents disclosed herein, but don't exclude other contents.

Compared with the prior art, the advantages of the present invention is as follows:

The invention has the advantages of short reaction steps, simple operation, no metal catalyst, no need of low temperature, and is suitable for industrial production.

EXAMPLES

The new preparation methods of PARP inhibitor talazoparib and intermediates thereof are disclosed in the examples of the present disclosure. Those skilled in the art can learn from this article to properly improve the process parameters to implement the preparation method. It's noted that all the similar replacements and changes are obvious for the skilled person and within the scope of the present disclosure. The methods disclosed herein are described in the preferred examples. Related persons can clearly realize and apply the techniques disclosed herein by making some changes, appropriate alterations or combinations to the methods without departing from spirit, principles and scope of the present disclosure.

In order to further understand the invention, it is detailed below through examples.

Example 1

Preparation of Compound 16

Compound 14 (100 g, 591 mmol), compound 15 (107.68 g, 591 mmol) and dioxane (1000 ml) were added into a first reactor, then PPTS (60.82 g, 118.2 mmol) and MgSO$_4$ (355.77 g, 2.96 mol) were added into the first reactor, then the first reactor was heated to reflux and stirred for 3 hours, cooled down to 50° C. NaBH$_4$ (89.46 g, 2.36 mol) was added into the mixture and heated to 80° C., the first reactor was then stirred for 3 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (100 g, yield 53.3%).

LC-MS (ESI) m/z: 318 (M+H)$^+$.

Example 2

Preparation of Compound 16

Compound 14 (100 g, 591 mmol), compound 15 (118.4 g, 650 mmol) and dioxane (1000 ml) were added into a first reactor, then PPTS (60.82 g, 118.2 mmol) and MgSO$_4$ (355.77 g, 2.96 mol) were added into the first reactor, then the first reactor was heated to reflux and stirred for 4 hours, cooled down to 50° C. NaBH$_4$ (89.46 g, 2.36 mol) was added into the mixture and heated to 80° C., the first reactor was then stirred for 4 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (98.1 g, yield 52.3%).

Example 3

Preparation of Compound 16

Compound 14 (100 g, 591 mmol), compound 15 (140 g, 768.3 mmol) and dioxane (1000 ml) were added into a first reactor, then PPTS (60.82 g, 118.2 mmol) and MgSO$_4$ (355.77 g, 2.96 mol) were added into the first reactor, then the first reactor was heated to reflux and stirred for 2 hours, cooled down to 50° C. NaBH$_4$ (89.46 g, 2.36 mol) was added into the mixture and heated to 80° C., the first reactor was then stirred for 2 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (95.5 g, yield 50.9%).

Example 4

Preparation of Compound 16

Compound 14 (100 g, 591 mmol), compound 15 (107.68 g, 591 mmol) and dioxane (1000 ml) were added into a first reactor, then PPTS (45.6 g, 88.65 mmol) and MgSO$_4$ (355.77 g, 2.96 mol) were added into the first reactor, then the first reactor was heated to reflux and stirred for 3 hours, cooled down to 50° C. NaBH$_4$ (89.46 g, 2.36 mol) was added into the mixture and heated to 80° C., the first reactor was then stirred for 3 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (96.0 g, yield 51.2%).

Example 5

Preparation of Compound 16

Compound 14 (100 g, 591 mmol), compound 15 (107.68 g, 591 mmol) and dioxane (1000 ml) were added into a first reactor, then PPTS (91.23 g, 177.3 mmol) and MgSO$_4$ (355.77 g, 2.96 mol) were added into the first reactor, then the first reactor was heated to reflux and stirred for 3 hours, cooled down to 50° C. NaBH$_4$ (89.46 g, 2.36 mol) was added into the mixture and heated to 80° C., the first reactor was then stirred for 3 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (97.6 g, yield 52.0%).

Example 6

Preparation of Compound 16

Compound 14 (100 g, 591 mmol), compound 15 (107.68 g, 591 mmol) and dioxane (1000 ml) were added into a first reactor, then PPTS (60.82 g, 118.2 mmol) and MgSO$_4$ (284.6 g, 2.368 mol) were added into the first reactor, then the first reactor was heated to reflux and stirred for 3 hours, cooled down to 50° C. NaBH$_4$ (89.46 g, 2.36 mol) was added into the mixture and heated to 80° C., the first reactor was then stirred for 3 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (94.8 g, yield 50.5%).

Example 7

Preparation of Compound 16

Compound 14 (100 g, 591 mmol), compound 15 (107.68 g, 591 mmol) and dioxane (1000 ml) were added into a first reactor, then PPTS (60.82 g, 118.2 mmol) and MgSO$_4$ (426.9 g, 3.552 mol) were added into the first reactor, then the first reactor was heated to reflux and stirred for 3 hours, cooled down to 50° C. NaBH$_4$ (89.46 g, 2.36 mol) was added into the mixture and heated to 80° C., the first reactor was then stirred for 3 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (95.3 g, yield 50.8%).

Example 8

Preparation of Compound 16

Compound 14 (100 g, 591 mmol), compound 15 (107.68 g, 591 mmol) and dioxane (1000 ml) were added into a first reactor, then PPTS (60.82 g, 118.2 mmol) and MgSO$_4$ (355.77 g, 2.96 mol) were added into the first reactor, then the first reactor was heated to reflux and stirred for 3 hours, cooled down to 50° C. NaBH$_4$ (67.1 g, 1.77 mol) was added into the mixture and heated to 80° C., the first reactor was then stirred for 3 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (97.7 g, yield 52.1%).

Example 9

Preparation of Compound 16

Compound 14 (100 g, 591 mmol), compound 15 (107.68 g, 591 mmol) and dioxane (1000 ml) were added into a first reactor, then PPTS (60.82 g, 118.2 mmol) and MgSO$_4$ (355.77 g, 2.96 mol) were added into the first reactor, then the first reactor was heated to reflux and stirred for 3 hours, cooled down to 50° C. NaBH$_4$ (111.8 g, 2.95 mol) was added into the mixture and heated to 80° C., the first reactor was then stirred for 3 hours. After the reaction, the first reactor was cooled down to room temperature, methanol was added into the first reactor and white solid was filtered. The filtrate was concentrated and extracted by ethyl acetate, then washed with saturated NaHCO$_3$ aqueous solution and sodium chloride aqueous solution. The organic phase was dehydrated with anhydrous sodium sulfate, filtered and concentrated to obtain crude product. The crude product was purified by column chromatography to give compound 16 (96.4 g, yield 51.4%).

Example 10

Preparation of Compound 17

Compound 16 (100 g, 315 mmol), absolute ethyl alcohol (1000 ml) and D(−)-tartaric acid (26 g, 173 mmol) were added into a second reactor, then the second reactor was heated to reflux for 2 hours and then cooled down to obtain white solid. The white solid was filtered off and washed with ethyl alcohol and saturated sodium bicarbonate aqueous solution. The organic phase was dehydrated with anhydrous sodium sulfate, filtered and concentrated to give compound 17 (46 g, yield 46%, ee % 97%).

LC-MS (ESI) m/z: 318 (M+H)$^+$.

Example 11

Preparation of Compound 17

Compound 16 (100 g, 315 mmol), absolute ethyl alcohol (1000 ml) and D(−)-tartaric acid (24.6 g, 164 mmol) were added into a second reactor, then the second reactor was heated to reflux for 2 hours and then cooled down to obtain white solid. The white solid was filtered off and washed with ethyl alcohol and saturated sodium bicarbonate aqueous solution. The organic phase was dehydrated with anhydrous sodium sulfate, filtered and concentrated to give compound 17 (44 g, yield 44%, ee % 96%).

Example 12

Preparation of Compound 17

Compound (100 g, 315 mmol), absolute ethyl alcohol (1000 ml) and D(−)-tartaric acid (46.4 g, 308.7 mmol) were added into a second reactor, then the second reactor was heated to reflux for 2 hours and then cooled down to obtain white solid. The white solid was filtered off and washed with ethyl alcohol and saturated sodium bicarbonate aqueous solution. The organic phase was dehydrated with anhydrous sodium sulfate, filtered and concentrated to give compound 17 (43 g, yield 43%, ee % 95%).

Example 13

Preparation of Compound 13

Compound 17 (46 g, 145 mmol) was dissolved in anhydrous tetrahydrofuran (500 mL) at room temperature and stirred, then sodium alcoholate (14.8 g, 217.4 mmol) was added into a third reactor. The third reactor was heated to reflux and stirred for 1.5 hours. Compound 18 (17.04 g, 145 mmol) was dissolved in tetrahydrofuran (200 mL) and added into the third reactor. The third reactor was stirred for 3 hours and cooled down to room temperature. Water was added into the system under ice-bath and the resulting mixture was extracted by ethyl acetate, then washed with saturated sodium bicarbonate aqueous solution and sodium chloride aqueous solution. The organic phase was dehydrated with anhydrous sodium sulfate, filtered and concentrated to give compound 13 (36 g, yield 62.3%).

LC-MS (ESI) m/z: 399 (M+H)$^+$.

$^1$H-NMR (400 MHz, DMSO-d$_6$) δ (ppm): 3.56 (s, 3H), 3.86 (s, 3H), 7.02 (dd, 2H), 7.2 (dd, 2H), 7.90 (s, 1H), 8.08 (s, 1H), 8.26 (dd, 1H), 8.56 (dd, H).

Example 14

Preparation of Compound 13

Compound 17 (46 g, 145 mmol) was dissolved in anhydrous tetrahydrofuran (500 mL) at room temperature and stirred, then sodium alcoholate (9.97 g, 146.5 mmol) was added into a third reactor. The third reactor was heated to reflux and stirred for 1 hour. Compound 18 (20.45 g, 174 mmol) was dissolved in tetrahydrofuran (200 mL) and added into the third reactor. The third reactor was stirred for 2 hours and cooled down to room temperature. Water was added into the system under ice-bath and the resulting mixture was extracted by ethyl acetate, then washed with saturated sodium bicarbonate aqueous solution and sodium chloride aqueous solution. The organic phase was dehydrated with anhydrous sodium sulfate, filtered and concentrated to give compound 13 (34 g, yield 58.9%).

Example 15

Preparation of Compound 13

Compound 17 (46 g, 145 mmol) was dissolved in anhydrous tetrahydrofuran (500 mL) at room temperature and stirred, then sodium alcoholate (19.74 g, 290 mmol) was added into a third reactor. The third reactor was heated to reflux and stirred for 2 hours. Compound 18 (25.56 g, 232 mmol) was dissolved in tetrahydrofuran (200 mL) and added into the third reactor. The third reactor was stirred for 4 hours and cooled down to room temperature. Water was added into the system under ice-bath and the resulting mixture was extracted by ethyl acetate, then washed with saturated sodium bicarbonate aqueous solution and sodium chloride aqueous solution. The organic phase was dehydrated with anhydrous sodium sulfate, filtered and concentrated to give compound 13 (33 g, yield 57.1%).

Example 16

Preparation of Talazoparib

Compound 13 (36 g, 90.37 mmol), ethanol (450 mL) and 50% hydrazine hydrate (28.96 g, 452 mmol) were added into a fourth reactor and heated to reflux for 3 hours. Then the solvent was removed by distillation under reduced pressure and the crude product was washed with water, filtered, washed with ethanol and recrystal to obtain the final product of compound 1 (talazoparib, white solid, 31 g, yield 90.2%), HPLC purity: 99.5%.

LC-MS (ESI) m/z: 381(M+1)$^+$.

$^1$H-NMR (400 MHz, DMSO-d$_6$): δ (ppm): 3.68 (s, 3H), 4.99-5.06 (m, 2H), 6.92-6.96 (m, 1H), 7.08-7.11 (m, 1H), 7.16-7.2 (t, J=8.8 Hz, 2H), 7.49-7.53 (m, 2H), 7.75 (s, 1H), 7.83 (s, 1H), 12.35 (s, 1H).

Example 17

Preparation of Talazoparib

Compound 13 (36 g, 90.37 mmol), ethanol (450 mL) and 50% hydrazine hydrate (23.17 g, 361.6 mmol) were added into a fourth reactor and heated to reflux for 4 hours. Then the solvent was removed by distillation under reduced pressure and the crude product was washed with water, filtered, washed with ethanol and recrystal to obtain the final product of compound 1 (talazoparib, white solid, 30.6 g, yield 89.0%), HPLC purity: 99.1%.

Example 18

Preparation of Talazoparib

Compound 13 (36 g, 90.37 mmol), ethanol (450 mL) and 50% hydrazine hydrate (34.75 g, 542.4 mmol) were added into a fourth reactor and heated to reflux for 2 hours. Then the solvent was removed by distillation under reduced pressure and the crude product was washed with water, filtered, washed with ethanol and recrystal to obtain the final product of compound 1 (talazoparib, white solid, 30.8 g, yield 89.6%), HPLC purity: 99.3%.

In the specification, unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing talazoparib of formula 1, comprising steps of:
    (1) contacting a compound of formula 14 with a compound of formula 15 to obtain a compound of formula 16;
    (2) contacting the compound of formula 16 with D(−)-tartaric acid to obtain a compound of formula 17;
    (3) contacting the compound of formula 17 with a compound of formula 18 to obtain a compound of formula 13; and
    (4) contacting the compound of formula 13 with 50% hydrazine hydrate to obtain the compound of formula 1,

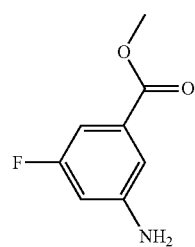

14

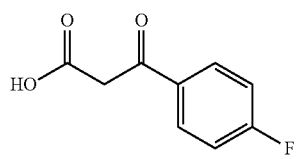

15

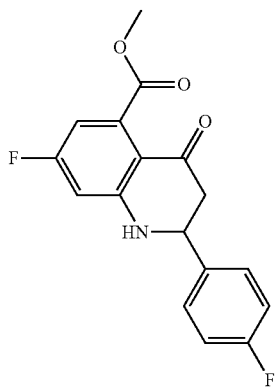

16

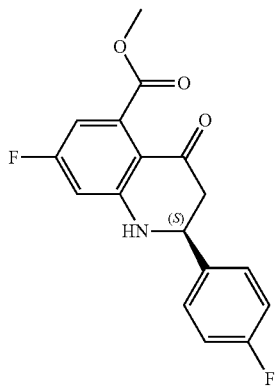

17

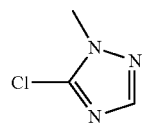

18

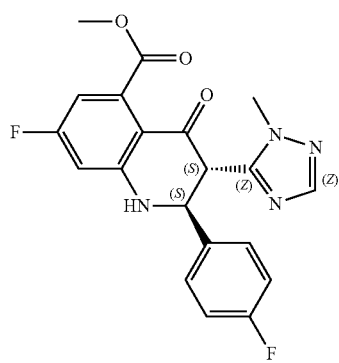

13

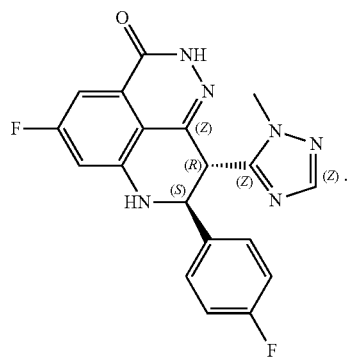

1

2. The method according to claim 1, wherein in the step (1), the compound of formula 14, the compound of formula 15 and dioxane are added into a first reactor, then pyridinium p-toluenesulfonate (PPTS) and $MgSO_4$ are added into the first reactor, then the first reactor is heated to reflux and stirred for 2 hours to 4 hours, cooled down to 50° C.; $NaBH_4$ is added into the mixture and heated to 80° C., the first reactor is then stirred for 2 hours to 4 hours; after the reaction, the first reactor is cooled down to room temperature, methanol is added into the first reactor and white solid is filtered; the filtrate is concentrated and extracted by ethyl acetate, then washed with saturated $NaHCO_3$ aqueous solution and sodium chloride aqueous solution; the organic phase is dehydrated with anhydrous sodium sulfate, filtered and concentrated to obtain crude product; and the crude product is purified by column chromatography to give compound 16.

3. The method according to claim 2, wherein the amount of compound 15 is 1.0 equivalent to 1.3 equivalents per 1 equivalent by mole of the compound of formula 14.

4. The method according to claim 2, wherein the amount of PPTS is 0.15 equivalent to 0.3 equivalent per 1 equivalent by mole of the compound of formula 14.

5. The method according to claim 2, wherein the amount of $NaBH_4$ is 3 equivalents to 5 equivalents per 1 equivalent by mole of the compound of formula 14.

6. The method according to claim 2, wherein the amount of $MgSO_4$ is 4 equivalents to 6 equivalents per 1 equivalent by mole of the compound of formula 14.

7. The method according to claim 1, wherein in the step (2), the compound of formula 16, absolute ethyl alcohol and D(−)-tartaric acid are added into a second reactor, then the second reactor is heated to reflux for 2 hours and then cooled down to obtain white solid; the white solid is filtered off and washed with ethyl alcohol and saturated sodium bicarbonate aqueous solution; the organic phase is dehydrated with anhydrous sodium sulfate, filtered and concentrated to give compound 17.

8. The method according to claim 7, wherein the amount of D(−)-tartaric acid is 0.52 equivalent to 0.98 equivalent per 1 equivalent by mole of the compound of formula 16.

9. The method according to claim 1, wherein in the step (3), the compound of formula 17 is dissolved in anhydrous tetrahydrofuran at room temperature and stirred, then sodium alcoholate is added into a third reactor; the third reactor is heated to reflux and stirred for 1 hour to 2 hours; the compound of formula 18 is dissolved in tetrahydrofuran and added into the third reactor; the third reactor is stirred for 2 hours to 4 hours and cooled down to room temperature; water is added into the system under ice-bath and the resulting mixture is extracted by ethyl acetate, then washed with saturated sodium bicarbonate aqueous solution and sodium chloride aqueous solution; the organic phase is dehydrated with anhydrous sodium sulfate, filtered and concentrated to give compound 13.

10. The method according to claim 9, wherein the amount of sodium alcoholate is 1.01 equivalents to 2.0 equivalents per 1 equivalent by mole of the compound of formula 17.

11. The method according to claim 9, wherein the amount of the compound of formula 18 is 1 equivalent to 1.6 equivalents per 1 equivalent by mole of the compound of formula 17.

12. The method according to claim 1, wherein in the step (4), the compound of formula 13, ethanol and 50% hydrazine hydrate are added into a fourth reactor and heated to reflux for 2 hours to 4 hours; then the solvent is removed by distillation under reduced pressure and the crude product is washed with water, filtered, washed with ethanol and recrystal to give the talazoparib of formula 1.

13. The method according to claim 12, wherein the amount of 50% hydrazine hydrate is 4 equivalents to 6 equivalents per 1 equivalent by mole of the compound of formula 13.

* * * * *